(12) United States Patent
Guan et al.

(10) Patent No.: US 11,213,544 B2
(45) Date of Patent: Jan. 4, 2022

(54) APPLICATION OF ALGINIC ACID SULFATE IN PREPARATION OF DRUGS AND HEALTH CARE PRODUCTS FOR PREVENTING AND TREATING DISEASES CAUSED BY HUMAN PAPILLOMA VIRUSES

(71) Applicant: MARINE BIOMEDICAL RESEARCH INSTITUTE OF QINGDAO CO., LTD., Shandong (CN)

(72) Inventors: Huashi Guan, Shandong (CN); Shixin Wang, Shandong (CN); Wei Wang, Shandong (CN); Chunxia Li, Shandong (CN); Pengli Li, Shandong (CN); Hongguang Wang, Shandong (CN); Xuan Xia, Shandong (CN); Xiaoshuang Zhang, Shandong (CN)

(73) Assignee: MARINE BIOMEDICAL RESEARCH INSTITUTE OF QINGDAO CO., LTD., Qingdao (CN)

(*) Notice: Subject to any disclaimer, the term of this patent is extended or adjusted under 35 U.S.C. 154(b) by 0 days.

(21) Appl. No.: 16/082,215

(22) PCT Filed: Feb. 28, 2017

(86) PCT No.: PCT/CN2017/075130
§ 371 (c)(1),
(2) Date: Sep. 4, 2018

(87) PCT Pub. No.: WO2017/148363
PCT Pub. Date: Sep. 8, 2017

(65) Prior Publication Data
US 2019/0343870 A1 Nov. 14, 2019

(30) Foreign Application Priority Data
Mar. 3, 2016 (CN) .................. 201610118796.X

(51) Int. Cl.
*A61K 31/737* (2006.01)
*A61P 31/20* (2006.01)
*A61K 9/46* (2006.01)
*A61K 9/02* (2006.01)

(52) U.S. Cl.
CPC .......... *A61K 31/737* (2013.01); *A61K 9/0007* (2013.01); *A61K 9/02* (2013.01); *A61P 31/20* (2018.01)

(58) Field of Classification Search
CPC .............. A61P 31/12–22; A61P 31/734; A61P 31/737; A61K 9/0034; A61K 9/0036; A61K 9/02; A61K 31/734; A61K 31/737
See application file for complete search history.

(56) References Cited

U.S. PATENT DOCUMENTS

| | | | | | |
|---|---|---|---|---|---|
| 2002/0172714 | A1* | 11/2002 | DiPiano | ............... | A61K 9/0034 424/489 |
| 2003/0181415 | A1* | 9/2003 | Zaneveld | ............. | A61K 9/0034 514/54 |

FOREIGN PATENT DOCUMENTS

CN 105748506 7/2016

OTHER PUBLICATIONS

Wang, S. et al "Potential anti-HPV and related cancer agents . . . " Mar. Drugs, vol. 12, pp. 2019-2035. (Year: 2014).*
Wang, W. et al "The antiviral activities and mechanisms of marine polysaccharides . . . " Mar. Drugs, vol. 10, pp. 2795-2816. (Year: 2012).*
Saha, S. et al "Sulfated polysaccharides from Laminaria angustata . . . " Carbohyd. Polym., vol. 87, pp. 123-130. (Year: 2012).*
Cruz, L. et al "Differntial dependence on host cell glycosaminoglycans . . . " Plos One, vol. 8, issue 7, pp. 1-11. (Year: 2013).*
Freeman, I. et al "The effect of sulfation of alginate hydrogels . . . " Biomaterials, vol. 29, pp. 3260-3268. (Year: 2008).*
Tian Youyun et al., Progress in Research on Brown Seaweed in Medicine and Food, Marine Science Bulletin, Jun. 1996, 6 pages, vol. 15—No. 3, abstract only.

* cited by examiner

*Primary Examiner* — Leigh C Maier
(74) *Attorney, Agent, or Firm* — Muncy, Geissler, Olds & Lowe, P.C.

(57) ABSTRACT

An application of alginate sulfate in the preparation of drugs and health care products for preventing and treating diseases caused by human papillomavirus. Alginate sulfate has a strong dose-dependent inhibitory effect on HPV infection through experiments, and alginate sulfate inhibited the expression of E6 and E7 genes and proteins in HPV-transformed Hela and Caski cells in a dose-dependent manner. The alginate sulfate can be developed into a drug or a health care product against human papillomavirus by systematic scientific experiments, which will have a good market application prospect.

13 Claims, 3 Drawing Sheets

APPLICATION OF ALGINIC ACID SULFATE IN PREPARATION OF DRUGS AND HEALTH CARE PRODUCTS FOR PREVENTING AND TREATING DISEASES CAUSED BY HUMAN PAPILLOMA VIRUSES

TECHNICAL FIELD

This invention belongs to the field of medical technology, and particularly relates to the application of alginate sulfate in the preparation of drugs and health care products for preventing and treating diseases caused by human papillomavirus.

TECHNICAL BACKGROUND

Human papillomavirus (HPV), as a sexually transmitted common pathogen, is one of the major viruses that threaten the health of modern people. HPV contains more than 100 types, and some of them can cause various lesions. There are 13 high-risk types and 5 low-risk types that mainly cause diseases. There is a correlation between the infection of high-risk HPV and the occurrence of tumors in some anal and genital areas.

Long-term infection of HPV16 and HPV18 subtypes has been identified as a major cause of cervical cancer. Currently, there are no specific anti-viral drugs for HPV in the market, and HPV vaccines are mainly adapted to women who have no sexual activity. Thus, the development of novel anti-HPV drugs with high efficiency is of great significance.

Because the proliferation of HPV depends on the differentiation of epithelial cells, it is substantially incapable of surviving in vitro. It is currently believed that the production of pseudoviruses is the most effective method to simulate HPV infection. HPV expresses capsid proteins L1 and L2 in mammalian cells. These two proteins have the ability to self-assemble into virus-like particles (VLPs) and encapsulate viral genomes or foreign genes in vitro to form pseudoviruses (PsV) which is consistent to the natural viral structure and immunogenicity. Professor Buck of the NIH in the United States reported that by using the characteristics of PsV to non-specifically package DNA, the plasmids expressing HPV L1 and L2 genes and the reporter plasmid can be co-transfected into mammalian cells and assembled into pseudoviral particles encapsulating the reporter plasmid. The pseudovirus constructed by this method has a higher titer, and the experimental operation is simple, and the result is stable and reliable. Therefore, the HPV pseudovirus system is currently widely used for screening and identification of anti-HPV vaccines and drugs. In addition, HPV-transformed cells such as Hela and Caski are also used for screening and pharmacodynamic evaluation of anti-HPV drugs.

Cervical cancer is one of the most common gynecological malignancies. In recent years, the incidence rate has increased year by year, and the age of onset has gradually become younger. Studies have shown that continuous or repeated infection of the human papillomavirus (HPV) is a major risk factor for cervical intraepithelial neoplasia and cervical cancer. In recent years, cervical HPV infection has received extensive attention. A large number of studies have confirmed that high-risk HPV infection is an important cause of cervical precancerous lesions and cervical cancer, which seriously threatens women's life and health. The key to preventing cervical cancer and recurrence and blocking the course of disease is to clear HPV. HPV is a non-enveloped small DNA virus that is classified into high-risk and low-risk depending on its carcinogenic strength. High-risk types include HPV16, 18, 31, 33, 35, 39, 45, 51, 52, 56, 58, 59, 68, etc., mainly causing CINII, III and cervical cancer. After high-risk HPV infects cervixes, the viral DNA is randomly integrated into the host cell genomic DNA; the E2 gene of the self-replicating inhibitory expression fragment is lost, the E6 and E7 oncogenes are overexpressed, and the E6 and E7 proto-oncoproteins bind to the tumor suppressor p53 and pRb in the host cell, respectively, and inactivate the tumor suppressor. The activation of proto-oncogene or inactivation of tumor suppressor gene can make cervical epithelial cells become malignant. After years of clinical research, it has been established that HPV infection is the main cause of cervical cancer and cervical intraepithelial neoplasia. Hybrid capture second generation (HCII) is currently the only FDA-approved HPV DNA detection technology that can simultaneously detect 13 high-risk types HPV without the need for gene amplification, with a negative predictive value of 99%.

For the prevention and treatment of cervical HPV, developed countries such as Europe and the United States have included preventive vaccines in the national routine vaccination, and in China vaccines have entered the second phase clinical trial, but preventive vaccines cannot cover all high-risk HPV types, and have no therapeutic effect on women with HPV infection-related types. Therapeutic vaccines for HPV-infected people are still under development and have not been put into clinical use on a large scale. However, problems such as vaccine safety and immunogenicity need to be improved. Physical and surgical treatment is applied to HPV-infected patients who have developed precancerous lesions of the cervix, but there may still be persistent HPV infection after surgery. The research hotspots for cervical HPV treatment mainly focus on the development of antiviral drugs, immunopotentiators and external preparations, and have made great breakthroughs. However, the effects in human clinical trials are not satisfied. There are still no effective preventive and therapeutic measures in clinical practice. Drug therapy for cervical HPV infection commonly uses interferon such as Xin Fu Ning (a recombinant human interferon a2b vaginal effervescent capsule). Theoretically, interferon inhibits the replication and transcription of viral nucleic acids by inducing the production of enzymatically active antiviral proteins in target cells, but its efficacy and side effects are still controversial.

Therefore, timely and effective removal of HPV virus in infected patients can block precancerous lesions and cervical cancer of cervical epithelial cells to different degrees. However, currently there are no specific drugs for the treatment of HPV infection.

SUMMARY OF THE INVENTION

The present invention provides an application of alginate sulfate in the preparation of drugs and health care products for preventing and treating diseases caused by human papillomavirus. The invention illustrates that the alginate sulfate has a strong inhibitory effect on HPV infection through experiments, and has a technical prospect of developing a drug for preventing and treating diseases caused by human papillomavirus.

In order to achieve the above object, the present invention is implemented by the following technical solutions:

The present invention provides the use of alginate sulfate in the preparation of drugs and health care products for preventing and treating diseases caused by human papillomavirus.

Further, the alginate sulfate is a sulfated polysaccharide compound obtained by introducing sulfate groups at the C2 and C3 positions of alginic acid. The weight-average molecular weight is 6~100 kDa, the polymannuronic acid content is 5~95%, the polyguluronic acid content is 5~95%, and the sulfate substitution degree is 5~15%.

Further, the preparation method of the alginate sulfate is as follows: Formamide is added to the reactor, and then chlorosulfonic acid is added slowly, followed by the addition of oligomeric alginic acid. The mass ratio of oligomeric alginic acid to formamide is 1:4~12, and the mass ratio of oligomeric alginic acid to chlorosulfonic acid is 1:1~3; The mixture formed by mixing the above components is stirred at 50 to 90° C. for 1 to 5 hours; After the reaction is finished, the product is precipitated by alcohol, filtered, and washed, and the precipitate is collected. After the precipitate is dissolved in water, the sodium hydroxide solution is slowly added to convert the precipitate into a salt, and the pH of the solution is adjusted to 8~10; The solution was decolorized with activated carbon, precipitated and crystallized by methanol or ethanol, and dried to obtain the alginate sulfate.

Further, the diseases caused by human papillomavirus include cervical cancer, common warts, flat warts, condyloma acuminata, papilloma of the meat handler, verrucous epidermal dysplasia, Bowenoid papulosis, laryngeal papilloma and condyloma.

Further, the alginate sulfate has a strong inhibitory effect on HPV pseudovirus infection and is dose-dependent; the alginate sulfate has a completely inhibitory effect against HPV infection after 48 hours.

Further, the alginate sulfate has an inhibitory effect on the expression of the pathogenic factor E6 gene of HPV.

Further, the alginate sulfate has an inhibitory effect on the expression of the pathogenic proteins E6 and E7 of HPV.

Further, the alginate sulfate is formulated with a water-soluble matrix or a fat-soluble matrix to form an external formulation comprising alginate sulfate. The formulations include vaginal suppositories, effervescent suppositories, vaginal effervescent capsules, vaginal soft capsules, vaginal effervescent tablets, gels, and sponge suppositories.

Further, the water-soluble matrix is one or more of glycerin gelatin, polyethylene glycol, polyoxyethylene monostearate, and poloxamer; the fat-soluble matrix is a cocoa bean ester, a semi-synthetic or fully synthetic fatty acid glyceride.

Further, the alginate sulfate is formulated with a water-soluble matrix or a fat-soluble matrix to form a formulation comprising alginate sulfate. The formulations include creams, liniments, filming agents, creams, elixirs, lotions, cataplasms, sprays, and aerosols.

Further, the formulation further comprises one or more of a hardener, a thickener, an emulsifier, an absorption enhancer, a colorant, an antioxidant or a preservative;

The hardener is selected one or more from white wax, cetyl alcohol, and stearyl alcohol;

The thickener is selected one or more from hydrogenated castor oil, glyceryl monostearate, and aluminum stearate;

The emulsifier is selected one or more from soap, gum arabic, and sodium alkylbenzene sulfonate;

The absorption enhancer is selected from the group consisting of Tween 80 and/or Azone; The coloring agent is selected one or more from amaranth, carmine, citrine, soluble indigo, orange G, eosin, solferino, gallocyanine, and sultan blue;

The antioxidant is selected one or more from sodium hydrogen sulfite, sodium metabisulfite, sodium sulfite, sodium thiosulfate, ascorbic acid, citric acid, t-butyl p-hydroxyanisole (BHA), and t-butyl p-cresol (BHT);

The preservative is selected one or more from parabens, benzoic acid, sorbic acid, ethanol, benzyl alcohol, and phenylethyl alcohol.

The advantages and technical effects of the present invention are as follows. Alginate sulfate is a kind of sulfated polysaccharide drug obtained by degradation and chemical modification of alginate derived from brown algae, which has low toxic and side effects and is less likely to develop drug-resistance. The invention systematically observes the efficacy of alginate sulfate on anti-human papillomavirus (HPV) through comprehensively application of cell culture technology, pseudovirus model, immunology technology and molecular biology technology. The main content thereof is: (I) Inhibition of alginate sulfate on the infection process of HPV pseudovirus; (II) the interference of alginate sulfate on HPV replication determined by HPV-transformed cervical cancer cells. The results showed that: (1) Alginate sulfate had a strong inhibitory effect on the HPV pseudovirus infection process, and it was dose-dependent, and it completely inhibited HPV infection after the application after 48 hours; (2) Alginate sulfate inhibited the expression of the viral E6 genes in HPV-transformed Hela and Caski cells, which is in a dose-response relationship; (3) Alginate sulfate inhibited the expression of E6 and E7 proteins in HPV-transformed Hela and Caski cells, which is in a dose-response relationship.

In summary, the present invention demonstrates that alginate sulfate can be developed into a drug and a health care product against human papillomavirus by systematic scientific experiments, which will have a good market application prospect.

DETAILED DESCRIPTION OF THE INVENTION

Figure 1:
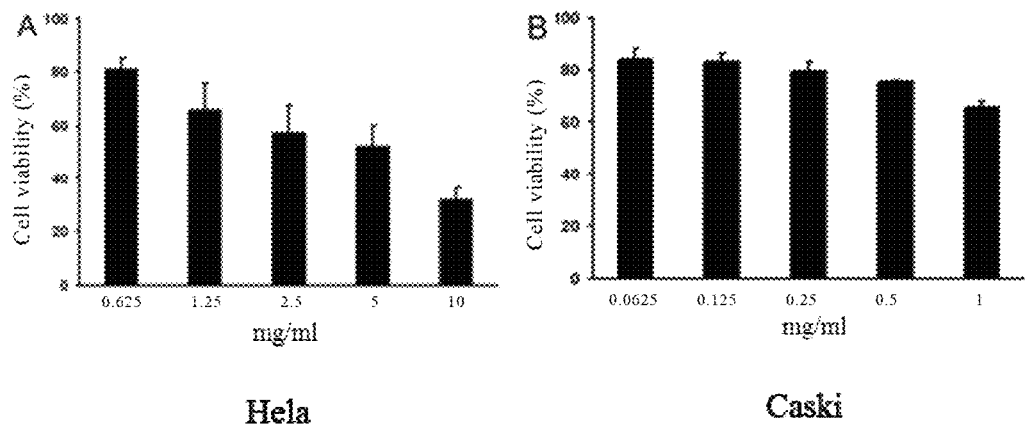
FIG. 1: The cytotoxicity of the alginate sulfate in Hela and Caski cells.
Figure 2:
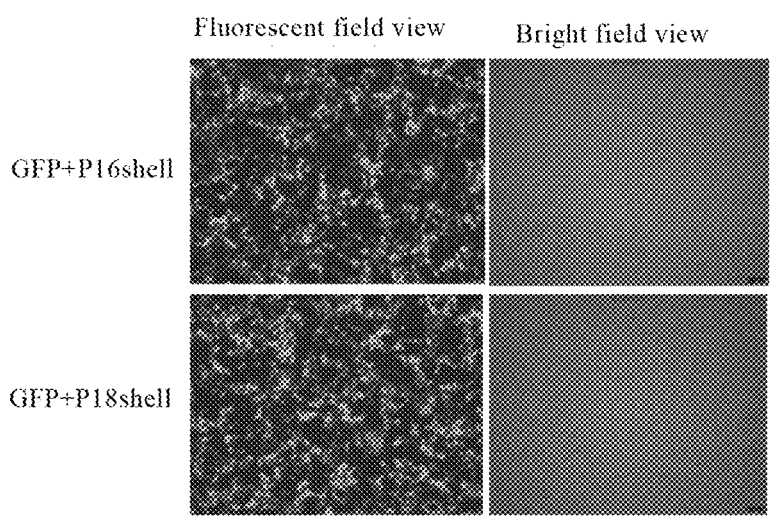
FIG. 2: Co-transfection of HPV 16 and 18 plasmids with GFP reporter plasmid in 293T/17 cells.

The technical solutions of the present invention are further described in detail below with reference to the accompanying drawings and specific embodiments.

Example 1

I. Inhibition Effects of Alginate Sulfate Against HPV Pseudovirus Infection (I) 293T/17 Cells and Hela/Caski Cells:

The 293 T/17 cell is an adenovirus-transformed embryonic kidney cell which can constitutively express the T antigen of the SV40 virus and is used as a packaging cell line in this invention. HeLa cells are human papillomavirus (HPV18) transformed cancer cells from normal cervical cells, and are infected by HPV pseudoviruses in this invention. After transfection with the plasmid of HPV capsid protein in 293 T/17 cells for 48 hours, the lysed cells were concentrated to collect the crude pseudovirus, and then purified to obtain the HPV pseudoviral particles. The HPV pseudoviral particles were used to infect Hela cells, and drugs were added to cells to determine the inhibitory effects on the HPV infection.

(II) Determination of the Test Drug and the Drug Dosage:

The alginate sulfate according to the present invention is a sulfated polysaccharide compound obtained by introducing sulfate groups ($-OSO_3^-$) at the C2 and C3 positions of oligo-alginic acid. The weight average molecular weight is 6~100 kDa, the polymannuronic acid (M segment) content is 5~95%, the polyguluronic acid (G segment) content is 5~95%, and the substitution degree of sulfate is 5~15%.

The preparation method of the alginate sulfate used in the embodiment is as follows: 500 kg of formamide was added to the sulfonation reactor, 135 kg of chlorosulfonic acid was slowly added dropwise, and 50 kg of oligomeric alginic acid was added after the dropwise addition was finished, and the temperature was further raised to 70° C. and reacted for 3 hours. After the reaction, the reaction product was precipitated by alcohol, and then the precipitate was washed and dissolved in water. The solution was dropwise added with sodium hydroxide solution until the pH drops to 8, decolorized with activated carbon, precipitated and crystallized by alcohol to obtain alginate sulfate.

The reaction formula of the preparation process is as follows:

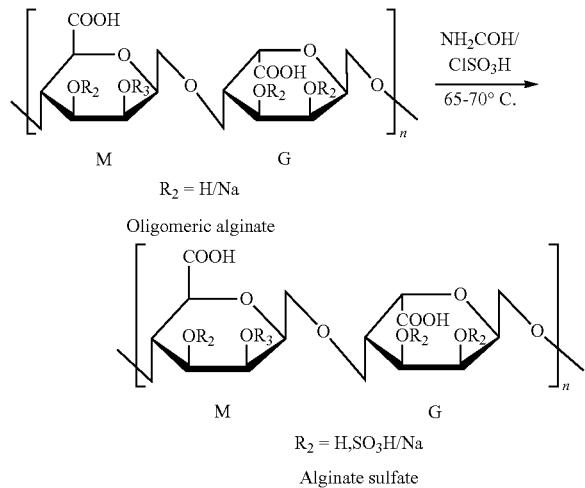

The determination of the drug dose is based on the provisions of the National Health and Family Planning Commission's "Preclinical Guideline Collections (Pharmacy, Pharmacology, Toxicology) of New Drug (Western Medicine)". The toxicity of the drug to Hela cells and Caski cells was determined at first, and the non-toxic concentration ($TD_0$) was calculated. The non-toxic concentration was serially diluted at 1:2 to produce 5 concentrations of the drug solution for antiviral experiments. Firstly, the alginate sulfate at a concentration of 100 mg/ml was prepared with the culture medium. After culturing of Hela cells or Caski cells for 24 hours, the drug solutions were diluted to 10, 5, 2.5, 1.25, 0.625 mg/ml, respectively. Then the drugs of different concentrations were added to 96-well culture plates with 3 wells per concentration, and the drug-free cell wells served as control. After incubation at 37° C. for 48 hours, the cell lesions were observed with a microscope, and the number of viable cells was evaluated by MTT method. The inhibition rate of cell proliferation per concentration of drug was calculated, and the median toxic concentration ($TD_{50}$) and the non-toxic dose ($TD_0$) were calculated according to the Reed Meuench method.

$$TD_{50}=Antilog[B+(50-<50\% \text{ inhibition percentage})\times C/(>50\% \text{ inhibition percentage}-<50\% \text{ inhibition percentage})]$$

($A=\log>50\%$ inhibition percentage, $B=\log<50\%$ inhibition percentage, $C=A-B$)

The results are shown in FIG. 1. After three repeated tests, the average median toxic concentration of the alginate sulfate to Hela cells was determined to be 4.044 mg/ml; the maximum non-toxic dose was 0.5 mg/ml; the average median toxic concentration of alginate sulfate to Caski cells was 8.473 mg/ml.

(III) Experimental Methods and Results:

1. 293T/17 Cells and Hela/Caski Cell Culture:

Add 0.25% trypsin to the cell-filled flask. The culture was incubated at 37° C. for 1 minute, and then it was gently mixed with medium, diluted at 1:3 and passaged. Two days later the cells were full and were added to a cell counter. The cell culture were prepared at 100,000 cells per ml, inoculated in the cell culture plates, with 0.1 ml per well of 96-well culture plate, 1 ml per well of 6-well plate. The plates were incubated in an incubator at 37° C. in an atmosphere of 5% $CO_2$ for 24 hours. Experiments were carried out when the cells grew into a single layer.

2. Plasmid Transfection and Production of HPV Pseudovirus:

Seven million 293T/17 cells were pre-plated in 75 cm² flasks and transfected after 16 hours. It is preferred to perform transfection when the cells spread about 40% of the flask. Firstly, 38 μg of HPV capsid protein plasmid and GFP reporter plasmid were mixed in 2 ml of OptiMEM, and 85 μl of liposome Lipofectamine 2000 was mixed in 2 ml of OptiMEM. After incubating respectively for 10 minutes at room temperature, the DNA and liposomes were mixed and incubated at room temperature for more than 20 minutes. The DNA-liposome mixture was added directly to the cells and incubated overnight at 37° C. The fresh DMEM medium was changed the next morning, and 20 ml of the medium was gently added from the cell-free side of the flask, and then cultured at 37° C. for 30 hours, and the whole process after transfection was 48 hours. The cells were harvested 48 hours after transfection, 1/20 volume of 10% Triton X-100 (final volume 0.5%) was added to the solution, and 0.1% Benzonase and 0.1% Plasmid Safe reagent were added. The cell lysate was then placed at 37° C. for 24 hours for the maturation process, and finally the cell lysate was dispensed and stored frozen at −80° C. for later use.

Figure 3:
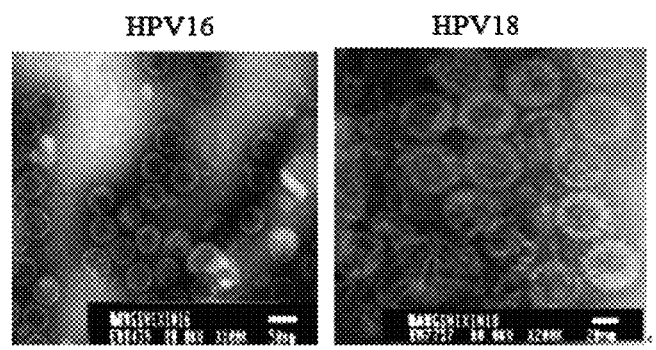
FIG. 3: Characterization of HPV 16 and 18 pseudovirions by transmission electron microscopy.

In order to confirm the assembly of the pseudovirus and the specific structure of the virion harvested, the fine structure was observed by transmission electron microscope (TEM). HPV is a regular dodecahedron with a diameter of 45-55 nm and no envelope surrounded. As shown in Figure. 3, the particle diameter of P16 or P18 assembled with GFP is about 45 nm, which is close to the natural virions, indicating that L1 and L2 can be assembled into mature virions.

3. Construction of HPV Pseudovirus Infection Model:

Hela cells were inoculated at 100,000 cells per ml in 96-well cell culture plates at 0.1 ml per well, and cultured in an incubator at 37° C. in an atmosphere of 5% $CO_2$ for 24 hours; Add 50 μl of 100-fold diluted HPV pseudoviral particle mixture to HeLa cells, and add 5 concentrations (125, 62.5, 31.25, 15.625, 7.8 μg/ml) of alginate sulfate diluted at 2-fold by the non-toxic concentration. The culture was incubated with 3 wells per concentration and the drug-free cell wells as blank control, and cultured in a 37° C. 5% $CO_2$ incubator for 48 hours. The culture solution was then discarded and washed twice with PBS. The cells were directly observed under a fluorescence microscope, and the fluorescence intensities of the cells between the dosing group and the blank control group were compared, and the number of positive cells (N) and the average optical intensity (AOI) were analyzed by Image J software, and the N and AOI were multiplied to get the relative amount of infection (RA=N×AOI), and the infection inhibition rate (%) was calculated.

Infection inhibition rate of HPV=($RA_{control}$−$RA_{sample}$)/$RA_{control}$

Figure 4:
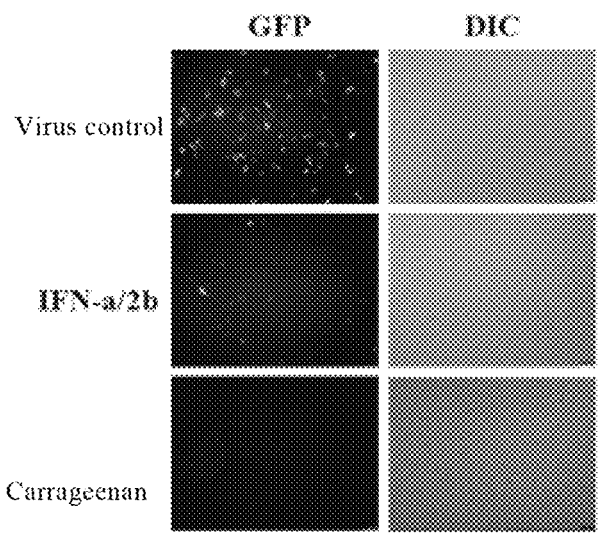
FIG. 4: The inhibitory effects of interferon and carrageenan against HPV16 pseudovirus infection.

The positive drug interferon α/2b and the compound carrageenan were used as controls. The results are shown in FIG. 4. The virus group had a strong fluorescence signal. After adding the positive drug IFN-α/2b (2.4 mg/ml, 3×10$^6$ U), the fluorescence intensity decreased, indicating that IFN-α/2b inhibited the expression of pseudovirus. The fluorescence intensity was significantly reduced after the addition of Iota-carrageenan (100 μg/ml). Since carrageenan is a currently reported potent compound that inhibits HPV pseudovirions, it sufficiently demonstrated that the HPV pseudovirus infection model was successfully constructed and is suitable for the screening of carbohydrate compounds.

4. Dose-Effect Relationship of Alginate Sulfate on Inhibition of HPV Pseudovirus Infection:

Hela cells were inoculated at 100,000 cells per ml in 96-well cell culture plates with 0.1 ml per well, and were cultured in a 37° C. 5% $CO_2$ incubator for 24 hours; Add 50 μl of 100-fold diluted HPV pseudoviral particle mixture to Hela cells. At the same time, different concentrations of alginate sulfate (7.8-125 μg/ml) were added to study the inhibitory effect on HPV pseudovirus infection with 3 wells per concentration. A virus well served as the control. The plates were cultured for 24 hours in a 37° C. 5% $CO_2$ incubator. The culture solution was then discarded and washed twice with PBS. The cells were directly observed under a fluorescence microscope, and the cell fluorescence intensities of the drug-treated group and the virus control group were compared.

Figure 5:
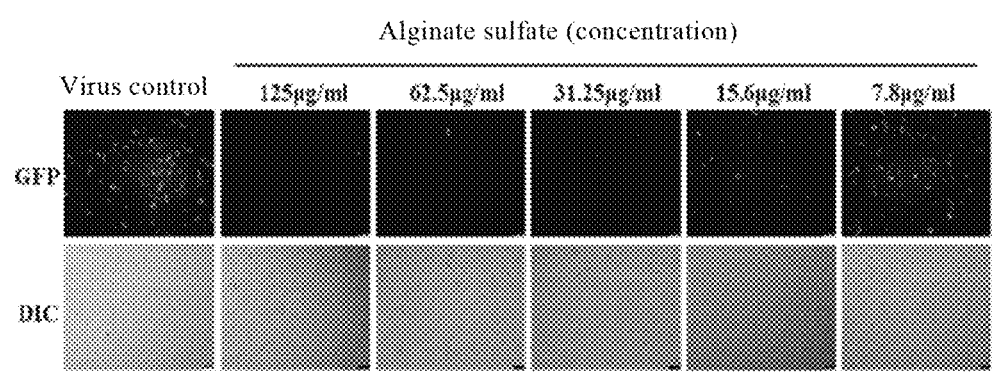
FIG. 5: The dose-effect relationship of the inhibition of HPV pseudovirus infection by the alginate sulfate.

The results showed that alginate sulfate almost completely inhibited the expression of GFP fluorescence when the concentration is above 31.25 μg/ml, while the expression of GFP was still inhibited at 7.8 μg/ml, but the number of positive cells did not change much. This indicates that the alginate sulfate showed a strong inhibitory effect on the HPV16 pseudoviral infection process, and the inhibition rate was as high as 73.8% at a lower concentration (15.625 μg/ml). The results are shown in FIG. 5 and Table 1-1.

TABLE 1-1

Inhibition of alginate sulfate on the infection process of HPV pseudovirus

| Groups | HPV16 Relative fluorescence intensity | HPV16 Average number of positive cells | HPV16 Relative infection | HPV16 Infection inhibition rate |
|---|---|---|---|---|
| Virus control group | 0.112 | 98 | 10.98 | — |
| Alginate sulfate-125 μg/ml | 0 | 0 | 0 | 100% |
| Alginate sulfate-62.5 μg/ml | 0.045 | 2 | 0.09 | 99.2% |
| Alginate sulfate-31.2 μg/ml | 0.05 | 8 | 0.4 | 96.4% |
| Alginate sulfate-15.6 μg/ml | 0.08 | 36 | 2.88 | 73.8% |
| Alginate sulfate-7.8 μg/ml | 0.074 | 71 | 5.254 | 52.1% |

4. Time-Effect Relationship of Inhibition of Alginate Sulfate Against HPV Pseudovirus Infection:

Hela cells were inoculated at 100,000 cells per ml in 96-well cell culture plates with 0.1 ml per well, and were cultured in a 37° C. 5% $CO_2$ incubator for 24 hours; Add 50 μl of a 100-fold diluted HPV pseudovirus particle mixture to HeLa cells. At the same time, 250 μg/ml of alginate sulfate solution was added to the plates with 3 wells per concentration, and virus wells served as the control, and the plates were cultured in a 37° C. 5% $CO_2$ incubator for 24, 48, 72, and 96 hours, respectively. The culture solution was then discarded and washed twice with PBS. The cells were observed under a fluorescence microscope by adding 200 μL of PBS, and the cell fluorescence intensities of the drug-treated group and the virus control group were compared.

Figure 6:
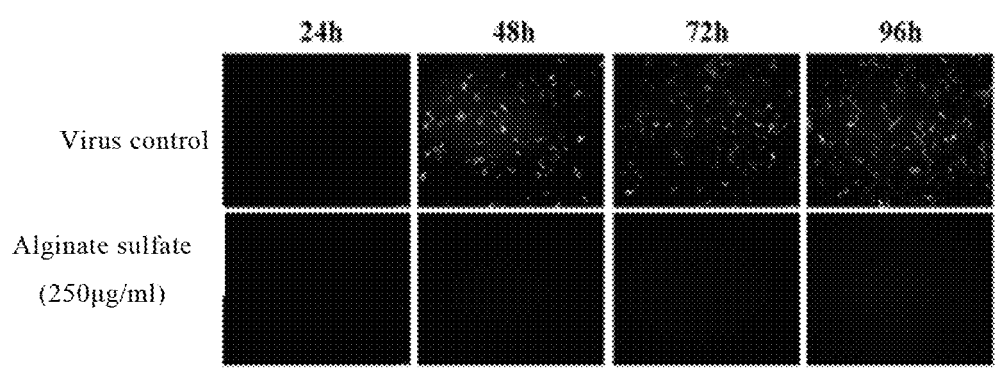
FIG. 6: The time-effect relationship of the inhibition of HPV pseudovirus infection by the alginate sulfate.

The experimental results are shown in FIG. 6. Except for GFP fluorescence was not expressed in 24 h, alginate sulfate (250 μg/ml) showed strong inhibition of HPV16 pseudoviral infection process at 48, 72, 96 hours. The inhibition rate was as high as 100%, and there was no decrease in potency. This indicates that the inhibition of HPV infection by alginate sulfate mainly occurs in the early stage of viral infection, and the efficacy is relatively long-lasting.

II. Interference Effects of Alginate Sulfate Against HPV Replication in HPV-Transformed Cervical Cancer Cells (I) Cervical Cancer Hela Cells and Caski Cells:

Both HPV18-transformed Hela cells and HPV16-transformed Caski cells are capable of expressing the E6 and E7 proteins of HPV. Different concentrations of the drug to be tested were added during the culture of Hela and Caski cells, the cells with different culture time were subjected to lysis, and the total RNA of the E6 gene in the cells was extracted for semi-quantitative RT-PCR to detect the inhibition of the E6 gene expression of HPV by the alginate sulfate. After the cells were lysed, western blot was used to detect the inhibitory effect of alginate sulfate on the expression of E6 and E7 protein in HPV, so as to determine the interference effect of the drug against viral replication.

(II) Experimental Methods and Results:

1. Hela Cells and Caski Cell Culture:

Add 0.25% trypsin to the flask filled with Hela or Caski cells, digest at 37° C. for 3-5 minutes, add medium to blow, dilute at 1:3, overgrown for two days, add to a cell counter to prepare a solution of 100,000 cells per ml. The cell culture was inoculated into cell culture plates with 0.1 ml per well in a 96-well culture plate, or with 1 ml per well in a 6-well plate, and was cultured in an incubator at 37° C. in an atmosphere of 5% $CO_2$ for 24 hours. Experiments were carried out when the cells grew into a single layer.

2. Inhibition of HPV E6 gene expression by drugs in Hela cells and Caski cell culture:

(1) RNA Extraction of HPV from HeLa Cells and Caski Cells:

One hundred thousand cells per ml were seeded in 6-well cell culture plates at 1 ml per well, and cultured in a 37-degree 5% $CO_2$ incubator for 24 hours; Add 3 concentrations (0.5, 0.25, 0.125 mg/ml) of alginate sulfate solution diluted 2-fold from the non-toxic concentration with 3 wells for each concentration, and set up a cell control well M. The plates were cultured in an incubator at 37° C. in an atmosphere of 5% $CO_2$ for 48 hours. The culture solution was then discarded and rinse twice with PBS. Add about 2 ml of Trizol to each well and mix well, and leaved at room temperature for 5 min for complete lysis. After centrifugation at 12,000 rpm at 4° C. for 5 min, the supernatant was aspirated, and the un-cracked precipitate was discarded. Add 200 μl of chloroform to 1 ml of Trizol cell lysate and mix thoroughly by inverting. Leave at room temperature for 15 min. Centrifuge at 12,000 rpm at 4° C. for 15 min. The upper aqueous phase was pipetted into a RNase-free eppendorf centrifuge tube treated with DEPC water. Mix the aqueous phase with isopropyl alcohol in a ratio of 1:1 and leave at room temperature for 5-10 min. After centrifugation at 12,000 rpm for 10 min at 4° C., the supernatant was discarded, and RNA was deposited on the bottom of the tube. Add 1 ml of 70% ethanol and gently suspend the precipitate by shaking. Centrifuge at 8,000 rpm at 4° C. for 5 min and discard the supernatant. Dry at room temperature for 5-10 minutes. RNA was dissolved by adding 20 μl of DEPC water per 1 ml of aqueous phase isopropanol precipitation. The RNA was stored at −80° C. in a freezer.

(2) Semi-Quantitative RT-PCR Detection of the Effect of Alginate Sulfate Against the E6 Gene in HPV-Transformed Cells:

The extracted total RNA was first reverse transcribed, using Oligo dT as a reverse primer, and the reaction system was 20 μl (including 4 μl of 5×RT Buffer, 1 μl of RT Enzyme Mix I, 1 μl of Oligo dT Primer (50 μM), 5 μl of Total RNA, 9 μl of RNase-free water), reverse transcription conditions: 37° C. for 15 min, 94° C. for 10 s. Then, the PCR reaction was carried out. The specific primer for the E6 gene of HPV was synthesized by Sangon Biotech (Shanghai) Co., Ltd. The reaction system was 30 μl (containing 3 μl of 10× Pyrobest PCR Buffer, 2.5 μl of dNTP (2.5 mmol/L), 0.6 μl of E6 gene upstream and downstream primers (20 mM), 3 μl of reverse transcribed cDNA product, 0.3 μl of Pyrobest DNA polymerase, 20 μl of sterile water). The PCR amplification cycle conditions were: 94° C. for 2 min; 94° C. for 40 s, 54° C. for 40 s, 72° C. for 40 s, for 30 cycles; extend at 72° C. for 2 min. After RT-PCR amplification, E6 was used as the target gene and β-actin was used as the internal reference. The change of E6 at the gene level was detected by agarose gel electrophoresis and quantitative analysis was performed. The DNA was semi-quantified by software, and the E6/actin ratio of the blank control was set to 1, and then E6/actin of each administration well was compared with the control well (ratio of 1), and the relative expression level (RF) of the E6 gene at each administration concentration was finally obtained, and the inhibition rate was calculated.

The inhibition rate of E6 gene expression of HPV=
($RF_{control}$−$RF_{sample}$)/$RF_{control}$.

Figure 7:
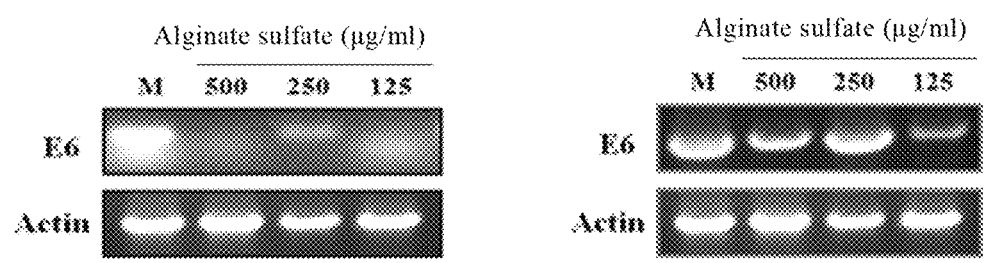
FIG. 7: The inhibitory effect of the alginate sulfate on the expression of the E6 gene of HPV.

The experimental results are shown in FIG. 7 and Table 1-2. The experimental results showed that the alginate sulfate drug groups showed inhibition of the expression of the main pathogenic factor E6 gene of HPV18 in Hela cells. The highest inhibition rate was 85% in the high dose (0.5 mg/ml) group and 74% in the middle dose (0.25 mg/ml) group; the low dose (0.125 mg/ml) group of alginate sulfate inhibited the expression of HPV16 E6 gene in Caski cells up to 70%, and the high dose (0.5 mg/ml) group was 48%.

TABLE 1-2

Inhibition of Alginate Sulfate on E6 Gene Expression of HPV in Hela Cells and Caski Cells

| Groups | E6/actin ratio in Hela cells | Relative inhibition rate in Hela cells | E6/actin ratio in Caski cells | Relative inhibition rate in Caski cells |
|---|---|---|---|---|
| Control group M | 1 | — | 1 | — |
| Alginate sulfate-500 μg/ml | 0.15 | 85% | 0.52 | 48% |
| Alginate sulfate-250 μg/ml | 0.26 | 74% | 1.09 | 0 |
| Alginate sulfate-125 μg/ml | 0.31 | 69% | 0.30 | 70% |

4. Inhibition of Drug on Expression of HPV E6 and E7 Proteins in Hela Cells and Caski Cell Culture:

One hundred thousand cells per ml were seeded in 6-well cell culture plates, 1 ml per well, and cultured in a 37° C. 5% $CO_2$ incubator for 24 hours; Add 2 times dilution of 3 concentrations (1.0, 0.5, 0.25 mg/ml) of alginate sulfate solution with 3 wells for each concentration, A cell control well M was set up. The plates were cultured for 48 hours in a 37° C. 5% $CO_2$ incubator. The culture solution was then discarded and washed twice with PBS. The RIPA cell lysate was added and lysed in an ice bath for 30 min. The cell lysate was collected in a 1.5 ml centrifuge tube and centrifuged at 4° C. 10,000 rpm for 10 min to precipitate. The supernatant was mixed with 2×SDS-PAGE loading buffer and then boiled in water for 5 min. After cooling, it was separated by SDS-PAGE electrophoresis. The expression of E6 and E7 protein in HPV was detected by western blot, and β-actin was used as an internal reference. The protein bands were quantified by Image J software, and the E6/actin or E7/actin ratio of the blank control was set to 1, and then the ratio of each administration well was compared with the control well (ratio of 1). The relative expression levels (RL) of the E6 and E7 proteins at each administered concentration were finally obtained, and the inhibition rate was calculated.

HPV E6 or E7 protein expression inhibition rate=
($RL_{control}$−$RL_{sample}$)/$RL_{control}$.

Figure 8:
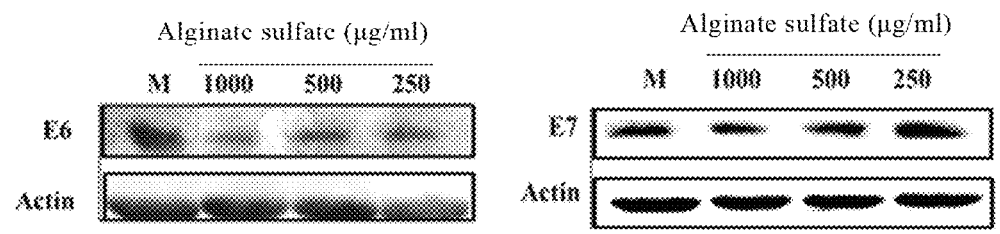
FIG. 8: The inhibitory effect of the alginate sulfate on the expression of E6 and E7 proteins of HPV.

The experimental results are shown in FIG. 8 and Table 1-3. The experimental results showed that each group of alginate sulfate showed an inhibitory effect on the protein expression of the main pathogenic protein E6 of HPV. The inhibition rate was 86% in the 1.0 mg/ml dose group and 65% in the medium dose (0.5 mg/ml) group; Alginate sulfate exhibited an inhibitory effect on the expression of E7 protein of HPV at a high dose (1.0 mg/ml) with an inhibition rate of 22%.

TABLE 1-3

Inhibition of alginate sulfate on the expression of E6 and E7 proteins in HPV

| Groups | E6/actin ratio in Hela cells | E6 inhibition rate in Hela cells | E7/actin ratio in Hela cells | E7 inhibition rate in Hela cells |
|---|---|---|---|---|
| Control group M | 1 | — | 1 | — |
| Alginate sulfate -1000 ug/ml | 0.14 | 86% | 0.78 | 22% |

TABLE 1-3-continued

Inhibition of alginate sulfate on the
expression of E6 and E7 proteins in HPV

| Groups | E6/actin ratio in Hela cells | E6 inhibition rate in Hela cells | E7/actin ratio in Hela cells | E7 inhibition rate in Hela cells |
|---|---|---|---|---|
| Alginate sulfate -500 ug/ml | 0.35 | 65% | 0.84 | 16% |
| Alginate sulfate -250 ug/ml | 0.57 | 43% | 1.16 | 0 |

In this example, the inhibitory effect of alginate sulfate on HPV pseudovirus infection process and the anti-HPV effect of alginate sulfate in HPV transformed cell culture were demonstrated by experiments, indicating that alginate sulfate has the effect of anti-human papillomavirus. As shown in the following table, the diseases caused by human papillomavirus are shown in Table 1-4, indicating that alginate sulfate has the application prospects for the prevention and treatment of cervical cancer, common warts, flat warts, condyloma acuminata, papilloma of the meat handler, dysplasia of the epidermis, laryngeal papilloma and genital warts.

TABLE 1-4

Viral pathology of HPV subtype

| HPV subtype | Viral pathology |
|---|---|
| HPV1 | Common warts (*verruca plantaris*) |
| HPV2 | Common warts (*verruca vulgaris*) |
| HPV3 | Flat wart, Verrucous epidermal dysplasia |
| HPV4 | Common warts (*Verruca plantaris*) |
| HPV5 | Flat wart, Verrucous epidermal dysplasia |
| HPV6 | Condyloma acuminata, Cervical cancer |
| HPV7 | Meat processor papilloma |
| HPV8 | Verrucous epidermal dysplasia (Malignant transformation) |
| HPV9 | Flat wart, Verrucous epidermal dysplasia |
| HPV10 | Flat wart, Verrucous epidermal dysplasia, Cervical cancer |
| HPV11 | Laryngeal papilloma and wet warts, Cervical cancer |
| HPV12 | Verrucous epidermal dysplasia |
| HPV13 | Oral epithelial local hyperplasia |
| HPV14 | Verrucous epidermal dysplasia |
| HPV15 | Verrucous epidermal dysplasia |
| HPV16 | Cervical cancer, Bowenoid papulosis |
| HPV18 | Cervical cancer |
| HPV31 | Cervical cancer |
| HPV33 | Cervical cancer |
| HPV45 | Cervical cancer |
| HPV58 | Cervical cancer |
| HPV59 | Cervical cancer |

Example 2: Preparation of Alginate Sulfate Suppository

The raw material for preparing the alginate sulfate suppository is the alginate sulfate powder, the semi-synthetic fatty acid glyceride, and glycerin. The specific preparation steps are as follows:

The alginate sulfate and the substrate are pulverized through a 100 mesh sieve. After matrix is melted under a water bath, alginate sulfate was added and stirred uniformly. After the temperature drops below 40° C., the mixture was poured into the mold. After cooling and solidifying, cut off the overflowed part by knife, open the plug mold, and push it out.

Example 3: Preparation of Alginate Sulfate Effervescent Suppository

The raw material for preparing the alginate sulfate effervescent suppository is the alginate sulfate powder, polyoxyethylene monostearate, sodium bicarbonate or liquid paraffin. The specific preparation steps are as follows:

All the excipients were dried at 105° C. for 2 h, and finely ground through an 80-mesh sieve for use. The polyoxyethylene monostearate is placed in a constant temperature water bath at 80° C., and after it is melted, the alginate sulfate is added. After fully stirring, add the effervescent agent and mix well, and the liquid wax is applied to the suppository mold, and the hot mixture is poured into the mold. After it is sufficiently cooled, the overflow portion is cut off and demolded.

The test data proves that the alginate sulfate has the effect of inhibiting HPV infection in the range of 6-18 kDa. The test proves that when the alginate sulfate is used to treat the disease caused by human papillomavirus, the functional group is sulfated M segment and G segment. The large molecular weight alginate sulfate is an increase of the functional-group sulfated M segment and G segment overlap units. Therefore, alginate sulfate in the range of 18 to 100 kDa also has a therapeutic effect on diseases caused by human papillomavirus.

In summary, alginate sulfate can significantly reduce the high-risk HPV viral load, improve the clinical symptoms of the cervix, treat cervical HPV infection significantly. It's safe and reliable in clinical use, and non-toxic side effects. It can be developed into a suppository or ointment for the treatment of cervical cancer and various skin blemishes.

The above embodiments are only used to illustrate the technical solutions of the present invention, and are not limited thereto. Although the present invention has been described in detail with reference to the foregoing embodiments, those skilled in the art can still modify the technical solutions described in the foregoing embodiments, or equivalently replace some of the technical features. But these modifications and substitutions do not depart from the spirit and scope of the technical solutions claimed in the present invention.

The invention claimed is:

1. A method for inhibiting expression of pathogenic E6 and/or E7 proteins of HPV in an HPV-transformed cell, which comprises contacting alginate sulfate with an HPV-transformed cell to inhibit the expression of pathogenic E6 and/or E7 proteins, wherein the alginate sulfate is a sulfated polysaccharide compound obtained by introducing sulfate groups at the C2 and C3 positions of alginic acid, a weight average molecular weight is 6-100 kDa, a polymannuronic acid content is 5-95%, a polyguluronic acid content is 5-95%, and a sulfate substitution degree is 5-15%.

2. The method of claim 1, wherein the alginate sulfate is prepared as follows: formamide is added into a reactor, and then chlorosulfonic acid is added slowly, followed by the addition of oligomeric alginic acid; a mass ratio of oligomeric alginic acid to formamide is 1:4~12, and a mass ratio of oligomeric alginic acid to chlorosulfonic acid is 1:1~3; the mixture formed by mixing the above components is stirred at 50 to 90 ° C. for 1 to 5 hours; after the reaction is finished, the product is precipitated by alcohol, filtered, and washed, and the precipitate is collected; after the precipitate is dissolved in water, a sodium hydroxide solution is slowly added to convert the precipitate into a salt, and a pH of the solution is adjusted to 8~10; the solution was decolorized with activated carbon, precipitated and crystallized with methanol or ethanol, and dried to obtain the alginate sulfate.

3. The method of claim 1, wherein the alginate sulfate has a weight average molecular weight of 6-18 kDa.

4. The method of claim 1, wherein the alginate sulfate has a sulfate substitution degree of 15%.

5. The method of claim 3, wherein the alginate sulfate is prepared by a method comprising the following steps:
adding 500 kg of formamide into a sulfonation reactor;
slowly adding dropwise 135 kg of chlorosulfonic acid;
adding 50 kg of oligomeric alginic acid after the dropwise addition is finished;
raising temperature to 70° C. and reacting for 3 hours, thereby obtaining a reaction product;
precipitating the reaction product by adding alcohol, thereby obtaining a precipitate;
washing the precipitate and dissolving the precipitate in water, thereby forming a solution;
adding dropwise a sodium hydroxide solution into the solution until pH drops to 8, thereby obtaining a first mixture;
decolorizing the first mixture with activated carbon, thereby obtaining a second mixture; and
conducting precipitation and crystallization of the second mixture by adding alcohol, thereby obtaining the alginate sulfate.

6. The method of claim 1, wherein the alginate sulfate is in a form of a formulation comprising alginate sulfate, wherein the formulation is selected from the group consisting of vaginal suppository, effervescent suppository, vaginal effervescent capsule, vaginal soft capsule, vaginal effervescent tablet, gel, and sponge suppository; wherein the water-soluble matrix is one or more materials selected from glycerin gelatin, polyethylene glycol, polyoxyethylene monostearate, and poloxamer; and the fat-soluble matrix is a one or more materials selected from cocoa butter, semi-synthetic or full-synthetic fatty acid glycerides.

7. The method of claim 1, wherein the alginate sulfate is in a form of a formulation comprising alginate sulfate; wherein the formulation includes cream, liniment, plastic, cream, tincture , lotion, cataplasm, spray, and aerosol.

8. The method of claim 7, wherein the formulation further comprises one or more components selected from the group consisting of a hardener, a thickener, an emulsifier, an absorption enhancer, a colorant, an antioxidant and a preservative.

9. The method of claim 8, wherein the hardener is selected from the group consisting of white wax, cetyl alcohol, and stearyl alcohol;
the thickener is selected from the group consisting of hydrogenated castor oil, glyceryl monostearate, and aluminum stearate;
the emulsifier is selected from the group consisting of soap, gum arabic, and sodium alkylbenzene sulfonate;
the absorption enhancer is selected from the group consisting of Tween 80 and/or Azone;
the coloring agent is selected from the group consisting of amaranth, carmine, citrine, soluble indigo, orange G, eosin, solferino, gallocyanine, and sultan blue;
the antioxidant is selected from the group consisting of sodium hydrogen sulfite, sodium metabisulfite, sodium sulfite, sodium thiosulfate, ascorbic acid, citric acid, t-butyl p-hydroxyanisole, and t-butyl p-cresol; and/or
the preservative is selected from the group consisting of paraben, benzoic acid, sorbic acid, ethanol, benzyl alcohol, and phenylethyl alcohol.

10. The method of claim 1, wherein the alginate sulfate is administered as a pharmaceutical composition.

11. The method of claim 1, wherein the subject is a human.

12. The method of claim 1, wherein the HPV-transformed cell is Hela cell or Caski cell in which the HPV virus is absent.

13. The method of claim 2, wherein the mass ratio of oligomeric alginic acid to chlorosulfonic acid is 1:3.

* * * * *